United States Patent
Hammer et al.

(12) 
(10) Patent No.: US 6,191,153 B1
(45) Date of Patent: Feb. 20, 2001

(54) USE OF 2-AMINO-6-N-PROPYL-AMINO-4,5,6, 7-TETRAHYDROBENZOTHIAZOLE AS A PHARMACEUTICAL COMPOSITION HAVING AN ANTIDEPRESSANT ACTIVITY

(75) Inventors: Rudolf Hammer, Ingelheim am Rhein; Joachim Mierau, Mainz; Erich Lehr, Waldalgesheim, all of (DE); Franco Borsini, Prate (IT)

(73) Assignee: Boehringer Ingelheim KG, Ingelheim (DE)

( * ) Notice: Under 35 U.S.C. 154(b), the term of this patent shall be extended for 0 days.

(21) Appl. No.: 09/526,079

(22) Filed: Mar. 15, 2000

Related U.S. Application Data

(63) Continuation of application No. 08/454,332, filed on Dec. 2, 1993, now abandoned.

(30) Foreign Application Priority Data

Dec. 5, 1992 (DE) .................................. 42 41 013
Dec. 2, 1993 (WO) .................................. PCT/EP93/03389

(51) Int. Cl.⁷ .................................. A61K 31/425
(52) U.S. Cl. .................................. 514/367
(58) Field of Search .................................. 514/367

(56) References Cited

FOREIGN PATENT DOCUMENTS 38 43 227   7/1990  (DE) .
0 186 087   7/1986  (EP) .
0 417 637   3/1991  (EP) .

OTHER PUBLICATIONS

Benkert, et al; "Dopamine Autoreceptor Agonists in the Treatment of Schizophrenia and Major Depression"; Pharmacopsychiatry; 1992; 25/6; pp. 254–260.

Brooks, et al; "The Pharmacology of Pramipexole in the Spontaneously Hypertensive Rat"; European J. Pharmacology, 200; 1991; pp. 339–341.

Borsini, et al; "Is the Forced Swimming Test a Suitable Model for Revealing Antidepressant Activity?"; Psychopharmacology 94; 1988; pp. 147–160.

Carter, et al; "Pramipexole, A Dopamine D2 Autoreceptor Agonist, Decreases, the Extracellular Concentration of Dopamine In Vivo"; Eur. J. Pharmacol. Bd. 200, Nr. 1; 1991; pp. 65–72.

deGruyter, et al; "Praemenstruelles Syndrom"; W. Pschyrembel 'Klinisches Woerterbuch; 1981; p. 958.

*Primary Examiner*—James H. Reamer
(74) *Attorney, Agent, or Firm*—Timothy X. Witkowski; Alan R. Stempel; Robert P. Raymond

(57) ABSTRACT

The invention relates to the use of pramipexol as a pharmaceutical composition having an antidepressant activity.

2 Claims, No Drawings

USE OF 2-AMINO-6-N-PROPYL-AMINO-4,5,6, 7-TETRAHYDROBENZOTHIAZOLE AS A PHARMACEUTICAL COMPOSITION HAVING AN ANTIDEPRESSANT ACTIVITY

This application is a continuation of Ser. No. 08/454,332, filed Dec. 2, 1993, now abandoned.

The present invention relates to antidepressant agents. More particularly, it relates to the use of 2-amino-6-n-propyl-amino-4,5,6,7-tetrahydrobenzothiazole, particularly the (−)-enantiomer thereof, and the pharmacologically acceptable acid addition salts thereof as pharmaceutical compositions having an antidepressant activity.

The compounds referred to above are known in pharmaceutical compositions primarily for treating schizophrenia and Parkinson's disease. Details of the preparation of these compounds, the (−)-enantiomers of which are also referred to in the literature as SND 919 or pramipexol, can be found in European Patent Application EP-A 85 116 016.

Surprisingly, it has now been found that pramipexol and related compounds have antidepressant properties. Particularly significant in this context is that pramipexol has an unexpectedly low α-receptor affinity and thus has a highly selective activity whilst being extremely well tolerated. The previously unknown long duration of activity of pramipexol (half life 12.5 hours) and its unexpectedly high bioavailability of more than 80% have proved particularly advantageous in the use of this substance as an antidepressant.

According to one aspect of the invention, therefore, we provide the use of 2-amino-6-n-propyl-amino-4,5,6,7-tetrahydrobenzothiazole and the pharmacologically acceptable acid addition salts thereof for treating depression.

We further provide a method of treating depression in a human or animal subject which comprises administering to said subject an effective amount of a compound as defined above.

The antidepressant activity of pramipexol was demonstrated in preclinical trials in the "forced swimming test". Details of this behavioural test are described for example by Willner, Psychopharmacology 83, 1–16 (1984) and by Borsini and Meli, Psychopharmacology 94, 147–160 (1988).

Pramipexol (SND 919) was investigated on eight rats, by comparison with aminaptine, a known antidepressant. Both substances were dissolved in physiological saline solution and administered by parenteral route. The results are shown in Table 1.

TABLE 1

Investigation of SND 919 and aminaptine in the "forced swimming test"

| Compound | Dose mg/kg | Immobility time (sec.) |
|---|---|---|
| Saline solution | — | 208 ± 10 |
| SND 919 | 0.03 | 210 ± 14 |
| SND 919 | 0.10 | 165 ± 6 |
| SND 919 | 0.30 | 102 ± 17 |
| Aminaptine | 20.00 | 134 ± 19 |

The results obtained demonstrate that SND 919 is clearly superior to aminaptine.

2-amino-6-n-propyl-amino-4,5,6,7-tetrahydrobenzothiazole, particularly the (−)-enantiomer thereof, and the pharmacologically acceptable acid addition salts thereof can be given for the treatment of depression, in the form of conventional galenic preparations consisting essentially of an inert pharmaceutical carrier and an effective dose of the active substance, e.g. plain or coated tablets, capsules, lozenges, powders, solutions, suspensions, emulsions, syrups, suppositories, etc. A therapeutically active single dose for the indication discovered according to the invention is within the range from 0.1 to 30 mg, preferably from 1 to 5 mg. In addition to being administered by oral or intravenous route pramipexol may also be taken transdermally. Suitable release systems for this purpose are known from the prior art, e.g. European Patent Application 428 038.

EXAMPLE 1

Tablet Core Containing 5 mg of 2-amino-6-n-propyl-amino-4,5,6,7-tetrahydro-benzothiazole-dihydrochloride Composition:

1 tablet core contains:

| | |
|---|---|
| SND 919 | 5.0 mg |
| Lactose | 33.5 mg |
| Corn starch | 10.0 mg |
| Gelatine | 1.0 mg |
| Magnesium stearate | 0.5 mg |
| | 50.0 mg |

Method of Preparation

The mixture of the active substance with lactose and corn starch is granulated with a 10% aqueous gelatine solution through a 1 mm mesh screen, then dried at 40° C. and rubbed through the same screen once more. The granules thus obtained are mixed with magnesium stearate and compressed to form tablet cores. The procedure must be carried out in a darkened room.

Weight of core: 50 mg

Punch: 5 mm, convex

The tablet cores thus obtained are coated by known methods with a coating consisting essentially of sugar and talc. The finished coated tablets are polished with beeswax.

Weight of coated tablet: 100 mg

EXAMPLE 2

Drops Containing 5 mg of 2-amino-6-n-propyl-amino-4,5,6,7-tetrahydro-benzothiazole-dihydrochloride Composition:

100 ml of drops contain:

| | |
|---|---|
| Methyl-p-hydroxybenzoate | 0.035 g |
| n-Propyl-p-hydroxybenzoate | 0.015 g |
| Aniseed oil | 0.05 g |
| Menthol | 0.06 g |
| Pure ethanol | 10.0 g |
| SND 919 | 0.5 g |
| Citric acid | 0.7 g |
| Sodium phosphate sec. × 2H$_2$O | 0.3 g |
| Sodium cyclamate | 1.0 g |
| Glycerol | 15.0 g |
| Distilled water | ad 100.0 ml |

Method of Preparation:

The p-hydroxybenzoates, aniseed oil and menthol are dissolved in ethanol (solution I). The buffer substances, the active substance and sodium cyclamate are dissolved in distilled water and glycerol is added (solution II). Solution I is stirred into solution II and the mixture is made up to the specified volume with distilled water. The finished drops solution is filtered through a suitable filter. The drops solution must be prepared and bottled away from the light and under protective gas.

EXAMPLE 3

Suppositories Containing 10 mg of 2-amino-6-n-propyl-amino-4,5,6,7-tetrahydro-benzothiazole-dihydrochloride 1 suppository contains:

| | |
|---|---|
| SND 919 | 10.0 mg |
| Suppository mass (e.g. Witepsol W 45) | 1690.0 mg |
| | 1700.0 mg |

Method of Preparation:

The finely powdered substance is stirred into the molten suppository mass cooled to 40° C., using an immersion homogeniser. At 35° C. the mass is poured into slightly chilled moulds.

Weight of suppository: 1.7 g

EXAMPLE 4

Ampoules Containing 5 mg of 2-amino-6-n-propyl-amino-4,5,6,7-tetrahydro-benzothiazole-dihydrochloride 1 ampoule contains:

| | |
|---|---|
| SND 919 | 5.0 mg |
| Citric acid | 7.0 mg |
| Sodium phosphate sec. × 2H$_2$O | 3.0 mg |
| Sodium pyrosulphite | 1.0 mg |
| Distilled water ad 1.0 ml | |

Method of Preparation:

The buffer substances, active substance and sodium pyrosulphite are dissolved successively in water which has been decocted and cooled under $CO_2$ gas. The solution is made up to the specified volume with decocted water and filtered free from pyrogens.

Packaging: in brown ampoules under protective gas

Sterilisation: 20 minutes at 120° C.

The ampoule solution must be prepared and packaged in a darkened room.

EXAMPLE 5

Coated Tablets Containing 10 mg of 2-amino-6-n-propyl-amino-4,5,6,7-tetrahydrobenzothiazole-dihydrochloride 1 tablet core contains:

| | |
|---|---|
| SND 919 | 10.0 mg |
| Lactose | 35.5 mg |
| Corn starch | 12.0 mg |
| Gelatine | 1.0 mg |
| Magnesium stearate | 0.5 mg |
| | 59 mg |

Method of Preparation:

As in Example 1.

What is claimed is:

1. A method for treating depression in a human being which method comprises administering to a human being suffering from depression an antidepressant amount of 2-amino-6-n-propyl-amino-4,5,6,7-tetrahydrobenzothiazole or a pharmaceutically acceptable salt thereof.

2. A method for treating depression in a human being which method comprises administering to a human being suffering from depression an antidepressant amount of (−) 2-amino-6-n-propyl-amino-4,5,6,7-tetrahydrobenzothiazole or a pharmaceutically acceptable salt thereof.

* * * * *